(12) United States Patent
Koest

(10) Patent No.: US 7,708,406 B2
(45) Date of Patent: May 4, 2010

(54) REFRACTOMETER FOR DETERMINING THE REFRACTION PROPERTIES OF AN EYE

(75) Inventor: Gert Koest, Hannover (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 368 days.

(21) Appl. No.: 11/784,320

(22) Filed: Apr. 5, 2007

(65) Prior Publication Data

US 2007/0236664 A1    Oct. 11, 2007

(30) Foreign Application Priority Data

Apr. 11, 2006    (DE) .................. 10 2006 017 389

(51) Int. Cl.
*A61B 3/14* (2006.01)
(52) U.S. Cl. .................. 351/208; 351/206; 351/210; 351/211; 351/214
(58) Field of Classification Search .................. 351/208
See application file for complete search history.

(56) References Cited

U.S. PATENT DOCUMENTS

| | | | |
|---|---|---|---|
| 4,588,270 A * | 5/1986 | Tamaki | 351/212 |
| 4,761,070 A | 8/1988 | Fukuma | |
| 4,812,033 A * | 3/1989 | Ishikawa | 351/208 |
| 5,886,767 A | 3/1999 | Snook | |
| 6,033,071 A | 3/2000 | Clawson et al. | |
| 6,120,444 A * | 9/2000 | Miyakawa et al. | 600/401 |
| 6,309,068 B1 | 10/2001 | Kohayakawa | |
| 6,603,103 B1 * | 8/2003 | Ulrich et al. | 250/205 |
| 6,682,195 B2 * | 1/2004 | Dreher | 351/204 |
| 2003/0108350 A1 * | 6/2003 | Brauning | 396/661 |

FOREIGN PATENT DOCUMENTS

DE    456 169    2/1928

DE    197 19 694 A1    11/1998

(Continued)

OTHER PUBLICATIONS

European Patent Office Search Report for Application No. EP 07 00 3204, 8 pgs. (Jun. 27, 2007).

*Primary Examiner*—Jessica T Stultz
(74) *Attorney, Agent, or Firm*—Blakely, Sokoloff, Taylor & Zafman LLP

(57) ABSTRACT

The invention pertains to a refractometer (01) for determining the refraction properties of an eye (02) of a patient with an optical projection device (03) that comprises at least one light source (08) that produces a light pattern, wherein the light pattern of the projection device (03) can be projected on the retina of the eye (02) and focused thereon, with an optical viewing device (04) that comprises at least one photoelectric sensor (12), wherein the light pattern reflected on the retina of the eye (02) can be viewed through the cornea and the lens of the eye with the viewing device (4) and projected on the photoelectric sensor (12) in the form of an image pattern, with an evaluation device for evaluating the image pattern recorded by the photoelectric sensor (12) and deriving the refraction properties of the eye, and with a distance measuring device for determining the distance between the refractometer (01) and the patient. The distance measuring device (16, 17) makes it possible to measure the distance between the refractometer (01) and the eye (02).

22 Claims, 1 Drawing Sheet

FOREIGN PATENT DOCUMENTS

| | | |
|---|---|---|
| DE | 299 13 602 U1 | 11/1999 |
| DE | 101 53 397 A1 | 11/2001 |
| EP | 0 563 454 A1 | 10/1993 |
| EP | 0 962 184 A1 | 12/1999 |
| EP | 1 074 214 A1 | 2/2001 |
| EP | 1 308 128 A2 | 5/2003 |
| WO | WO 02/080760 A1 | 10/2002 |
| WO | WO 2004/037078 A1 | 5/2004 |

* cited by examiner

REFRACTOMETER FOR DETERMINING THE REFRACTION PROPERTIES OF AN EYE

FIELD

The invention pertains to a refractometer according to the preamble of Claim 1 for determining the refraction properties of an eye.

BACKGROUND

Refractometers of this type are also frequently referred to as autorefractors and serve for measuring the refraction of an eye and, if applicable, the ametropia thereof from a distance.

The basic principle of such refractometers is described in U.S. Pat. No. 4,761,070. A light pattern is produced with the aid of an optical projection device, for example, light-emitting diodes, and projected on the retina of the eye. The projection of the light pattern is realized such that the light pattern is focused on the retina. The light pattern reflected on the retina is viewed through the eye lens by means of an optical viewing device that comprises a photoelectric sensor, for example, a video camera, such that an image pattern is projected on the photoelectric sensor. This image pattern is recorded with the photoelectric sensor and evaluated with an evaluation device, preferably digital image data processing software. The light pattern projected on the retina is characteristically distorted in accordance with the refraction properties of the eye such that the refraction properties of the eye can be derived by evaluating the degree of distortion.

One important aspect for the correct derivation of the refraction properties is that the eye is arranged a certain distance from the refractometer. Deviations in the distance between the eye and the refractometer result in a correspondingly altered distortion of the light pattern on the photoelectric sensor such that these deviations lead to measuring errors in the determination of the refraction properties.

In order to prevent these measuring errors, DE 101 53 397 A1 describes a refractometer system that also features a measuring unit for determining the distance between the device and the patient. The data obtained from the distance measurement can be used for positioning the patient correctly in front of the device. It would therefore also be conceivable to incorporate the distance information into the evaluation and thusly correct the refraction measurement data accordingly.

Suitable measuring systems for determining this distance are described in DE 101 53 397 A1 and respectively consist of an ultrasonic transceiver and an optical distance measuring system, in which a light pattern is projected on the forehead of the person being examined in order to measure the distance between the forehead and the measuring system.

The disadvantage of the measuring device described in DE 101 53 397 A1 is that only the distance between the head of the patient and the refractometer can be measured. This measurement is therefore inaccurate and, in principle, does not suffice for suitably correcting the refractometer data because the position of the head does not contain definitive information on the position of the eye. The correction of the measuring data consequently leads to unsatisfactory results.

SUMMARY

Based in this state of the art, the present invention aims to propose a new refractometer with integrated distance measuring device that eliminates the disadvantages of the prior art.

This objective is attained with a refractometer according to the characteristics of Claim 1.

Advantageous embodiments of the invention from the objects of the dependent claims.

The fundamental idea of the invention is that the distance measuring device provided in the refractometer should be suitable for measuring the distance between the refractometer and the eye to be examined because only this distance is important for the correction of the measuring data. Only the utilization of this distance data that describes the distance between the eye and the refractometer makes it possible to respectively position the patient correctly or to properly correct the refraction measurement data.

The measuring accuracy can be improved if the distance measuring device makes it possible to measure the distance between the refractometer and the cornea of the eye, particularly the front surface of the cornea and/or the rear surface of the eye.

Alternatively or additionally, it is particularly advantageous if the distance measuring device also makes it possible to measure the distance between be refractometer and the lens of the eye, particularly the front surface of the lens and/or the rear surface of lens.

The distance measuring device may essentially be realized arbitrarily. It proved particularly advantageous with respect to the measuring accuracy to utilize a distance measuring device that comprises a slit projection device for the slit illumination of the eye and a Scheimpflug camera for recording split images of the eye. An evaluation of the image data of the split images recorded with the Scheimpflug camera makes it possible to derive the distance between the refractometer and the eye with extremely high accuracy. The evaluation of the split images also makes it possible to measure the distance to the front surface or the rear surface of the cornea as well as the distance to the front surface or the rear surface of the lens.

If the refractometer utilizes a Scheimpflug camera for the distance measurement, said camera may naturally also be utilized for carrying out conventional tacheometric measuring tasks. For example, it would also be possible to derive the thickness of the cornea tissue from of the split images.

In order to carry out a correct measurement, it is advantageous that the eye remains stationary during the measurement. This is the reason why it is particularly advantageous if a fixation marking is provided in the refractometer, wherein said fixation marking is fixed during the measurement of the eye so as to prevent undesirable eye movements.

In order to broaden the functional spectrum of the refractometer, a second optical projection device and a second optical projection device and a second optical viewing device may also be integrated into the refractometer, wherein the second optical projection device forms a keratometer in cooperation with the second optical viewing device and a suitable evaluation device. The measuring markings of the keratometer that form part of the projection device may essentially be realized arbitrarily. It is particularly preferred if two collimated light spots and an essentially circular, non-collimated light strip are provided as measuring markings in the projection device of the keratometer.

The collimated light spots are preferably produced with light-emitting diodes that are arranged in a tubular body, wherein lenses are respectively arranged in front of the light-emitting diodes.

The circular non-collimated light strip is preferably produced with an optical waveguide element in the shape of a circular cylinder. In this case, the light of an illuminating means is coupled into the optical waveguide element on the rear face and/or the cylinder circumference and emerges from the optical waveguide element on the front face. In this case, the illuminating means for the optical waveguide element in the shape of a circular cylinder may also consist of light-emitting diodes that are preferably distributed over the circumference of the optical waveguide element in the shape of a circular cylinder.

The light source used for producing the light pattern in the optical projection device of the refractometer may essentially be realized arbitrarily. Infrared light sources proved particularly advantageous in this respect.

A pin diaphragm is preferably provided in the optical viewing device of the refractometer.

The photoelectric sensors in the different viewing devices of the refractometer or the Scheimpflug camera or the keratometer may essentially be realized arbitrarily. It is preferred to utilize video sensors that convert the recorded image data into a video signal and forward the video signal to downstream functional units. It is particularly cost-efficient if the video sensors consist of chip cameras, particularly CCD cameras.

The video signal of the video sensor should preferably have a digital data format in order to easily process the digital image data.

A set-up camera or a view camera should be provided in the refractometer in order to easily align the eye to be examined before the beginning of the measurement and to view the eye during the examination. In a suitable arrangement, the set-up camera can be simultaneously used as a view camera during the measurement.

If a keratometer is integrated into the refractometer, the optical viewing device of the keratometer can also be used as a set-up camera or a view camera, respectively.

BRIEF DESCRIPTION OF THE DRAWINGS

One embodiment of the invention is schematically illustrated in the drawing and described in an exemplary fashion below.

In this drawing,

FIG. 1 schematically shows the beam path of a refractometer 01 for carrying out measurements on the eye 02.

DETAILED DESCRIPTION

Figure 1:
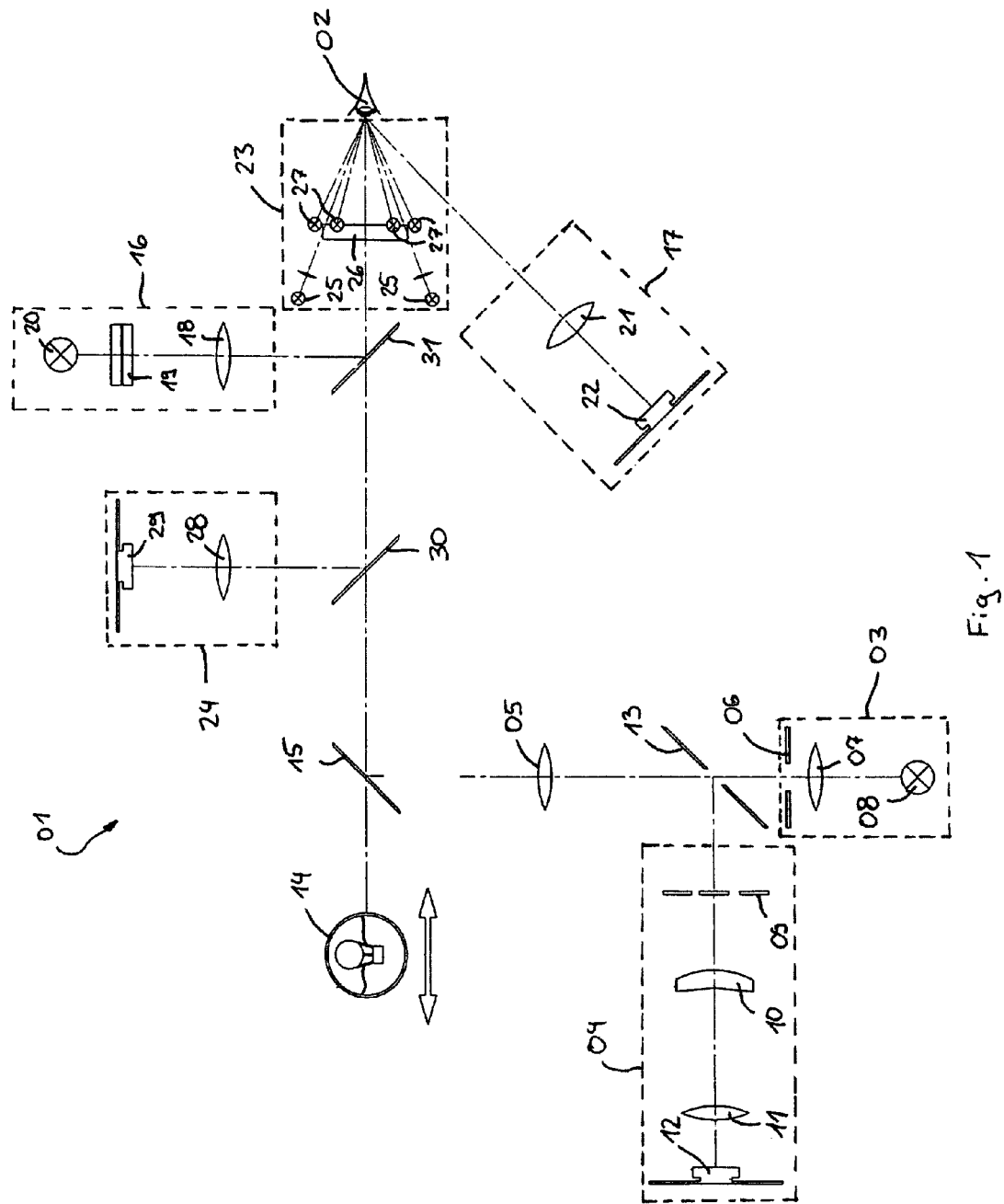
FIG. 1 shows the schematic design of one embodiment of a refractometer according to the invention.

An optical projection device 03 and an optical viewing device 04 that form an autorefractor in cooperation with an objective 05 and a not-shown evaluation device are used for determining the refraction properties of an eye 02. The optical projection device 03 makes it possible to project and focus a light pattern on the retina of the eye 02. In this case, the optical projection device 03 comprises a pin diaphragm 06, a lens 07 and an infrared light source 08. The optical viewing device 04 of the autorefractor comprises a sextuple pin diaphragm 09, a deflecting prism 10, an objective 11 and a CCD camera 12. The image data recorded with the CCD camera 12 are evaluated in the downstream evaluation device that is realized in the form of a digital image processing system in order to determine the refraction properties of the eye 02. A mirror 13 with pin diaphragm serves for coupling the different beam paths of the optical projection device 03 and the optical viewing device 04.

In order to fix the eye 02 while the measurement is carried out, the refractometer 01 furthermore comprises an adjustably supported fixation marking 14, the beam path of which is coupled by means of a separating plate 15.

In order to determine the distance of the eye 02 relative to the refractometer, a distance measuring device is provided that consists of a slit projection device 16 and a Scheimpflug camera 17. The slit projection device 16 and the Scheimpflug camera 17 are arranged in accordance with the Scheimpflug rule such that the split images recorded with the Scheimpflug camera 17 are suitable for determining the distance between the refractometer 01 and the eye 02 by means of image data analysis. The image data analysis of the split images of the eye 02 makes it possible, in particular, to determine the distance of the refractometer 01 to the cornea of the eye, particularly the front surface or rear surface of the cornea, as well as the distance of the refractometer 01 from the lens of the eye, particularly the front surface of the lens or the rear surface of the lens. In addition, the slit projection device 16 and the Scheimpflug camera 17 naturally can also be used for carrying out normal tacheometric measurements, particularly measurements of the thickness of the cornea. The slit projection device 16 comprises an objective 18, a slit diaphragm 19 and a slit lamp 20. The Scheimpflug camera 17 is arranged angularly relative to the eye 02 in accordance with the Scheimpflug rule and comprises an objective 21 and a CCD camera 22 that serves as the image recording device of the Scheimpflug camera.

In addition, a keratometer that consists of a suitable projection device 23 and an assigned optical viewing device 24 is also integrated into the refractometer 01. In the optical projection device, two light-emitting diodes 25 serve as collimated light spots. An optical waveguide element 26 with assigned LEDs serves as collimated light strip with circular-cylindrical geometry. An objective 28 and a CCD camera 29 are provided in the optical viewing device 24. The CCD camera 29 simultaneously serves as a set-up camera and viewing camera. Two separating plates 30 and 31 serve for coupling the beam paths of the slit projection device 16 and of the optical viewing device 24 of the keratometer.

LIST OF REFERENCE SYMBOLS

01 Refractometer
02 Eye
03 Optical projection device (autorefractor)
04 Optical viewing device (autorefractor)
05 Objective (autorefractor)
06 Pin diaphragm
07 Lens
08 Infrared light source
09 Pin diaphragm
10 Deflecting prism
11 Objective
12 CCD camera
13 Mirror with pin diaphragm
14 Fixation marking
15 Separating plate
16 Slit projection device
17 Scheimpflug camera
18 Objective
19 Slit diaphragm
20 Slit lamp
21 Objective
22 CCD camera
23 Optical projection device (keratometer)
24 Optical viewing device (keratometer)
25 LED
26 Optical waveguide in the shape of a circular cylinder
27 LED
28 Objective 29 CCD Camera
30 Separating plate
31 Separating plate

What is claimed is:

1. A refractometer for determining the refraction properties of an eye of a patient, comprising:
   an optical projection device that comprises at least one light source that produces a light pattern, wherein the light pattern of the projection device is projected on the retina of the eye and focused thereon,
   an optical viewing device that comprises at least one photoelectric sensor, wherein the optical viewing device views the light pattern reflected on the retina of the eye through the cornea and the lens of the eye and wherein the light pattern is projected on the photoelectric sensor in the form of an image pattern,
   an evaluation device for evaluating the image pattern recorded by the photoelectric sensor and deriving the refraction properties of the eye, and
   a distance measuring device for determining the distance between the refractometer and the patient, wherein the distance measuring device is able to measure the distance between the refractometer and the eye, and wherein the distance measuring device includes a slit projection device to illuminate the eye and a Scheimpflug camera to record split images of the eye, wherein the distance between the refractometer and the eye is derived from the split images of the eye.

2. The refractometer according to claim 1, wherein the distance measuring device is able to measure the distance between the refractometer and the cornea of the eye, particularly the front surface of the cornea and/or the rear surface of the cornea.

3. The refractometer according to claim 1, wherein the distance measuring device is able to measure the distance between the refractometer and the lens of the eye, particularly the front surface of the lens and/or the rear surface of the lens.

4. The refractometer according to claim 1, wherein the thickness of the cornea tissue can also be derived from the split images of the eye in an evaluation device.

5. The refractometer according to claim 1, wherein the refractometer includes a fixation marking that is fixed by the eye during a measurement.

6. The refractometer according to claim 5, wherein the actual or virtual distance between the eye and the fixation marking is variable.

7. The refractometer according to claim 6, wherein the actual distance between the eye and the fixation marking is varied by adjusting the fixation marking in the refractometer.

8. The refractometer according to claim 6, wherein the virtual distance between the eye and the fixation marking is varied by adjusting at least one lens in the beam path between the fixation marking and the eye.

9. The refractometer according to claim 1, wherein the refractometer includes a second optical protection device and a second optical viewing device that form a keratometer in cooperation with an evaluation device.

10. The refractometer according to claim 9, wherein a defined measurement marking is projected on the cornea with the projection device of the keratometer.

11. The refractometer according to claim 9, wherein the measurement marking features two collimated light spots and a non-collimated light strip that essentially has the shape of a circular cylinder.

12. The refractometer according to claim 11, wherein the collimated light spots are respectively produced by a light-emitting diode arranged in a tubular body, wherein at least one lens is arranged in front of the light-emitting diodes.

13. The refractometer according to claim 11, wherein the non-collimated light strip in the shape of a circular cylinder is produced with an optical waveguide element that has the shape of a circular cylinder, wherein the light of at least one illuminating means is coupled into the optical waveguide element on the rear face or the cylinder circumference and emerges from the optical waveguide element on the front face.

14. An analyzing system according to claim 13, wherein the illuminating means comprise several light-emitting diodes that are distributed over the circumference of the optical waveguide element in the shape of a circular cylinder.

15. The refractometer according to claim 1, wherein an infrared light source is provided in the optical projection device of the refractometer in order to produce the light pattern.

16. The refractometer according to claim 1, wherein a pin diaphragm is provided in the optical viewing device of the refractometer.

17. The refractometer according to claim 1, wherein at least one video sensor is respectively provided in the optical viewing device of the refractometer or in the Scheimpflug camera, wherein the video sensor forwards the image data in the form of a video signal.

18. The refractometer according to claim 17, wherein the video sensors comprise a chip camera.

19. The refractometer according to claim 17, wherein the video signal is generated in a digital data format or converted into a digital data format.

20. The refractometer according to claim 1, wherein a digital image processing system suitable for evaluating digital image data is used as the evaluation device of the refractometer or the Scheimpflug camera.

21. The refractometer according to claim 1, wherein the refractometer features a set-up camera for aligning the eye to be examined in the correct position or a view camera for viewing the eye to be examined during the examination.

22. The refractometer according to claim 9, wherein the optical viewing device of the keratometer can also be used as a set-up camera or a view camera.

* * * * *